US00PP20377P2

(12) United States Plant Patent
Cain

(10) Patent No.: US PP20,377 P2
(45) Date of Patent: Oct. 6, 2009

(54) GRAPEVINE 'IFG 104-253'

(50) Latin Name: *Vitis vinifera*
Varietal Denomination: IFG 104-253

(75) Inventor: David W. Cain, Bakersfield, CA (US)

(73) Assignee: International Fruit Genetics, LLC, Bakersfield, CA (US)

( * ) Notice: Subject to any disclaimer, the term of this patent is extended or adjusted under 35 U.S.C. 154(b) by 0 days.

(21) Appl. No.: 12/215,932

(22) Filed: Jun. 27, 2008

(51) Int. Cl.
*A01H 5/00* (2006.01)

(52) U.S. Cl. ..... Plt./205

(58) Field of Classification Search ..... Plt./205
See application file for complete search history.

*Primary Examiner*—Annette H Para
(74) *Attorney, Agent, or Firm*—Townsend and Townsend and Crew LLP

(57) ABSTRACT

This invention is a new and distinctive grapevine 'IFG 104-253'. 'IFG 104-253' produces naturally large, elongated white seedless berries that require little or no exogenous application of gibberellic acid to obtain commercially acceptable berry size which ripen in mid-season.

1 Drawing Sheet

Latin name of the genus and species of the plant claimed: *Vitis vinifera.*

Variety denomination: 'IFG 104-253'.

BACKGROUND OF THE INVENTION

The new and distinct grapevine described and claimed herein originated from a hand pollinated cross of the Princess variety (non-patented) and the Regal variety (South African PBR ZA971795) hybridized in May 2001. The abortive seed traces were subsequently embryo cultured and the resulting plant was planted in the field in April 2002. The present variety of grapevine was selected as a single plant in July 2003 and was first asexually propagated by hardwood cuttings in December 2003. The resulting propagules were planted during April 2004 near Delano, Kern County, Calif. and were found to reproduce true-to-type through at least three generations of asexual reproduction.

BRIEF SUMMARY OF THE INVENTION

The new grapevine 'IFG 104-253' is characterized by producing naturally large, elongated white seedless berries that require little or no exogenous application of gibberellic acid to obtain commercially acceptable berry size which ripen in mid-season.

To the inventor's knowledge, the known varieties to which the new grapevine variety is most similar are the parent varieties and the Sugraone variety (U.S. Plant Pat. No. 3,106) and the Sugratwelve (U.S. Plant Pat. No. 8,298) variety. 'IFG 104-253' can be distinguished from these varieties based on unique combination of characteristics, which include naturally large crisp, very uniform berries with both high visual attractiveness and high eating quality combined with viticultural characteristics that reduce growing costs compared to existing varieties. 'IFG 104-253' can further be distinguished based on the characteristics described below.

The new grapevine variety can be distinguished from its parent the Princess variety by having narrower, more elongated berries which are more uniform and less variable in size and shape. The new variety exhibits a much lower tendency to excessively yellow than the Princess variety when exposed to direct sunlight. The new variety exhibits no internal browning during storage which plagues the Princess variety. The new variety is less vigorous and more productive than the princess variety and does not exhibit reduced fruitfulness under low light conditions created by a heavy canopy of foliage. The new variety does not produce and muscat flavor when fully ripe as compared to the Princess variety which exhibits a mild muscat flavor when fully ripe.

'IFG 104-253' most closely resembles its parent variety the Regal Seedless in having a similar color and general shape. The new variety differs from the Regal Seedless by having a slightly more elongated berry shape, by having a slightly more waxy bloom giving it a more desirable and slightly less shiny appearance. It further differs from the Regal variety by having a more desirable broad shouldered conical cluster shape as opposed to the narrower more elongated cluster shape of the Regal variety. The new variety does not exhibit an astringent taste which sometimes plagues the Regal variety. The new variety has a more desirable crisp texture and superior eating quality as compared to the Regal variety. The new variety does not exhibit any internal browning during storage which plagues its parent the Regal variety. The new variety differs from the Regal variety by ripening five or more days before the Regal variety. The new variety has naturally loose clusters requiring less laborious hand or chemical thinning. The new variety requires little or no gibberellic application to attain commercially acceptable berry size compared to the Regal variety and the new variety exhibits less subsequent crop reduction if gibberellic acid is applied as compared with the Regal variety.

'IFG 104-253' differs from the Sugraone variety (U.S. Plant Pat. No. 3,106 expired) by ripening later and having more uniform and more elongated berries. The new variety produced heavily when pruned to two bud spurs as opposed to the Sugraone variety which required more costly pruning to long canes.

'IFG 104-253' differs from the Sugratwelve (U.S. Plant Pat. No. 8,298) by ripening after the Sugratwelve variety and by producing heavily when pruned to two bud spurs as opposed to the Sugratwelve variety which required more costly pruning to long can.

BRIEF DESCRIPTION OF THE DRAWINGS

The accompanying photographic illustration in FIG. 1 illustrates 'IFG 104-253'. The photograph was taken using conventional techniques. The colors are as nearly true as is reasonably possible in a color representation of this type.

DETAILED DESCRIPTION OF THE INVENTION

Figure 1:
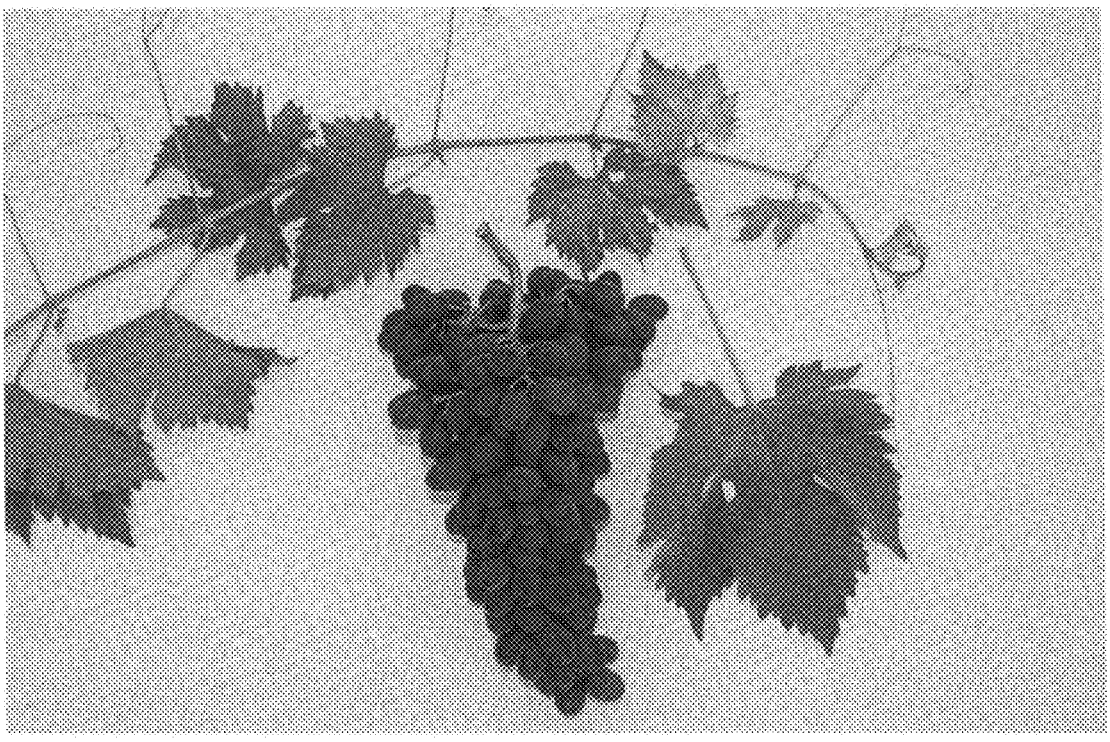
Figure 1:
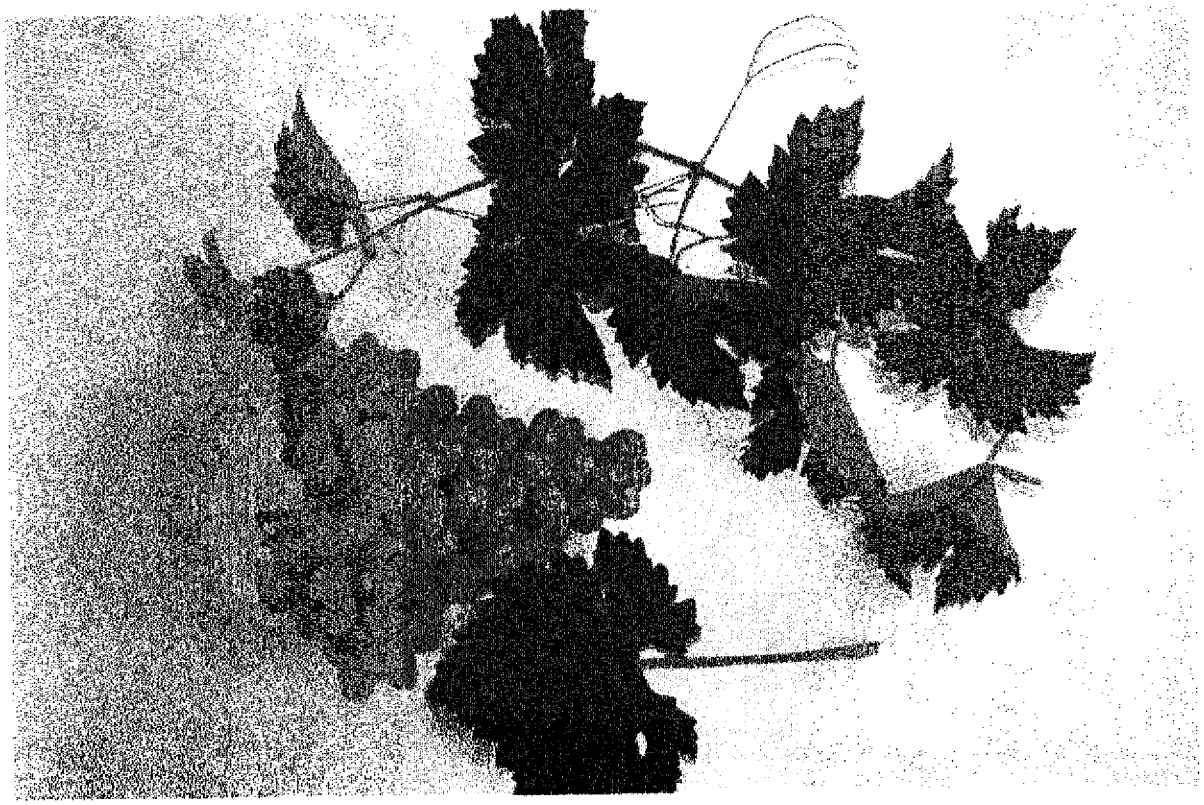
Figure 1:
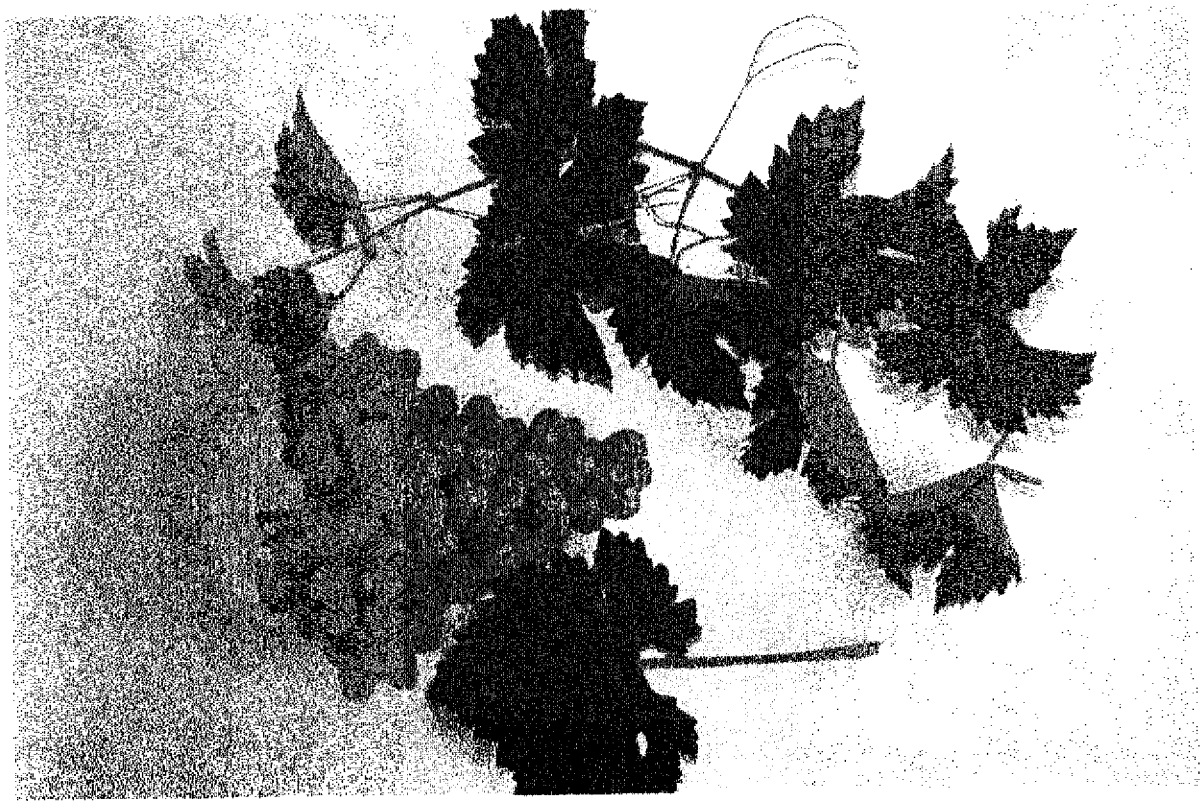

Throughout this specification, color names beginning with a small letter signify that the name of that color, as used in common speech, is aptly descriptive. Color names beginning with a capital letter designate values based upon R.H.S. Colour Chart, published by The Royal Horitcultural Society, London, England.

Throughout this specification subjective description values conform to those set forth by the International Plant Genetic Resources Institute publication 'Descriptors for Grape' (*Vitis* spp.) (1983) which was developed in collaboration with the Office International de la Vigne et du Vin (OIV) and the International Union for the Protection of New Varieties of Plants (UPOV).

The following descriptive matter pertains to 'IFG 104-253' plants grown in the vicinity of Delano, Kern County, Calif. during 2007 –2008, and is believed to apply to plants of the variety grown under similar conditions of soil and climate elsewhere.

VINE

General:
- *Size.*—Medium.
- *Vigor.*—Medium.
- *Density of foliage.*—Medium.
- *Productivity.*—Very productive.
- *Root stock.*—Own root.
- *Training method.*—Typically spur pruned leaving 2 bud spurs.

Trunk:
- *Trunk diameter of* 4-*year-old vines at* 30 *cm above the soil line.*—7.3 cm.
- *Shape.*—Medium.
- *Straps.*—Very long, split.
- *Surface texture.*—Shaggy.
- *Inner bark color.*—Greyed-Orange 174 A.

SHOOTS

Young shoot:
- *Form of tip.*—Wide open.
- *Distribution of anthocyanin coloration of tip.*—Absent.
- *Intensity of anthocyanin coloration of tip.*—Absent.
- *Density of prostrate hairs on tip.*—Very sparse.
- *Density of erect hairs on tip.*—Absent.
- *Color.*—Yellow Green 144 A.

Woody shoot (mature canes):
- *Shape.*—Medium.
- *Internode length.*—Medium to long ; about 132.5 mm.
- *Width at node.*—About 12 mm.
- *Cross section.*—Circular.
- *Surface.*—Striate.
- *Main color.*—Greyed-orange group; 166C.
- *Density of erect hairs of nodes.*—None or very sparse.
- *Density of erect hairs on internodes.*—None or very sparse.
- *Growth of axillary shoots.*—Medium; approximately 16.5 cm.

Flowering shoot:
- *Vigor during flowering.*—Medium.
- *Attitude during flowering on shoots not tied.*—Semi-drooping.
- *Color.*—Dorsal side of internodes — green with red stripes red.
- *Color.*—Ventral side of internodes — yellow green 144A.
- *Color.*—Dorsal side of nodes — yellow green 144A.
- *Color.*—Ventral side of nodes — yellow green 144A.
- *Density of prostrate hairs of nodes.*—None.
- *Density of erect hairs of nodes.*—None.
- *Density of prostrate hairs on internode.*—Absent.
- *Density of erect hairs on internode.*—Absent.
- *Anthocyanin coloration of buds.*—Absent.

Tendrils:
- *Distribution on the shoot* (*at full flowering*).—Discontinuous.
- *Length of tendril.*—Long; about 26.5 cm.
- *Thickness.*—Medium.
- *Color.*—Yellow green 144A.
- *Form.*—Trifurcated.
- *Number of consecutive tendrils.*—Three or more.

LEAVES

Young leaves:
- *Color of upper surface of first four distal unfolded leaves.*—Green 146 B.
- *Average intensity of anthocyanin coloration of six distal leaves prior to flowering.*—Absent.
- *Density of prostrate hairs between veins* (*lower surface*).—Absent.
- *Density of prostrate hairs on veins.*—Very sparse.
- *Density of erect hairs between veins* (*lower surface*).—Absent.
- *Density of erect hairs on veins.*—Very sparse.

Mature leaves:
- *Average length.*—About 14.7 cm.
- *Average width.*—About 15.8 cm.
- *Mature leaf size.*—Medium to large.
- *Shape of blade.*—Pentagonal.
- *Number of lobes.*—3.
- *Anthocyanin coloration of main veins on upper side of blade.*—Very weak.
- *Mature leaf profile.*—Involute.
- *Blistering surface of blade upper surface.*—Weak.
- *Leaf blade tip.*—In the plane of the leaf.
- *Undulation of margin.*—Pronounced.
- *Thickness.*—Medium.
- *Undulation of blade between main and lateral veins.*—Absent.
- *Shape of teeth.*—Both sides convex.
- *Length of teeth.*—Medium.
- *Ratio length/width of teeth.*—Small.
- *Shape of upper lateral sinuses.*—Open.
- *Depth of upper lateral sinuses.*—Shallow.
- *General shape petiole sinus.*—Slightly open.
- *Shape of base of upper leaf sinuses.*—V-shaped.

*Density of prostrate hairs between veins on lower surface of blade.*—Absent.
*Density if erect hairs between veins on lower surface of blade.*—Absent.
*Density of prostrate hairs on main veins on lower surface of blade.*—None or very sparse.
*Density of erect hairs on main veins on lower surface of blade.*—Sparse.
*Density of prostrate hairs on main veins on upper surface of blade.*—None or very sparse.
*Density of erect hairs on main veins on upper surface of blade.*—None.
*General shape petiole sinus.*—Half open.
*Shape of base of petiole sinus.*—U-shaped.
*Mature leaf tooth at petiole sinus.*—Absent.

Upper surface:
*Color.*—Green 137 B.
*Anthocyanin coloration of main veins.*—Absent.
*Surface appearance.*—Semi-glossy.
*Blistering surface of blade.*—Very weak.

Lower surface:
*Color.*—Yellow green 146 B.
*Anthocyanin coloration of main veins (lower surface).*—Absent.
*Glossiness.*—Medium.
*Surface texture.*—Smooth.
*Surface appearance.*—Semi-glossy.

Petiole:
*Length.*—About 11.4 cm.
*Length of petiole compared to middle vein.*—Slightly shorter.
*Density of prostrate hairs on petiole.*—None.
*Density of erect hairs on petiole.*—None.

Buds:
*Bud fruitfulness.*—Basal: mostly fruitful.
*Position of first fruitful shoot on previous season cane.*—1st to 2nd node.
*Time of bud burst.*—Mid season; Mar. 3, 2008 (measurement from a single location).

FLOWERS

General:
*Flower sex.*—Hermaphrodite.
*Length of first inflorescence.*—Long; approximately 15.2 cm.
*Position of first flowering and fruiting node.*—2nd to 3rd node (current season growth).
*Number of inflorescence per flowering shoot.*—1.1 to 2.
*Date of full bloom.*—May 10, 2007.
*Time of bloom.*—Medium as compared with similar varieties in the growing area of Kern County, Calif.

FRUIT

General:
*Ripening period.*—Medium; approximately Aug. 16, 2007 (measurement from a single location).
*Use.*—Fresh market.
*Keeping quality.*—Good.
*Resistance to.*—Insects: average typical of *Vitis vinifera* species. diseases: average typical of *Vitis vinifera* species.
*Refractometer test.*—Solid-sugar: about 18.2 brix.
*Brix/acid.*—About 20.7.
*Titratable acidity.*—About 0.88.
*Juice pH.*—About 3.1.

Cluster:
*Mature cluster length (peduncle excluded).*—About 22.3 cm.
*Mature cluster weight.*—About 1075 g.
*Bunch density.*—Medium.
*Number of berries.*—About 170.
*Form.*—Conical.

Peduncle:
*Length of peduncle.*—Approximately 5.7 cm.
*Lignification of peduncle.*—Weak.

Berry:
*Uniformity of size.*—Uniform.
*Single berry weight.*—About 8.2 g when treated with gibberellic acid.
*Shape.*—Elongated elliptic.
*Seed*—Rudimentary seed traces present, but very small.
*Dimensions.*—Longitudinal axis: About 3.4 cm. horizontal axis: about 1.6 cm.
*Skin color (without bloom).*—Yellow green 151A.
*Anthocyanin coloration of flesh.*—Absent.
*Berry firmness.*—Firm.
*Particular flavor.*—Neutral.
*Bloom (cuticular wax).*—Weak-medium.
*Berry separation from pedicel.*—Medium.

Skin:
*Thickness.*—Medium.
*Texture.*—Medium.
*Reticulation.*—Absent.
*Tenacity.*—Tenacious to flesh.

What is claimed is:

1. A new and distinct variety of grapevine plant having the characteristics substantially as described and illustrated herein.

* * * * *

UNITED STATES PATENT AND TRADEMARK OFFICE

CERTIFICATE OF CORRECTION

PATENT NO. : PP 20,377 P2
APPLICATION NO. : 12/215932
DATED : October 6, 2009
INVENTOR(S) : David W. Cain It is certified that error appears in the above-identified patent and that said Letters Patent is hereby corrected as shown below:

Drawing sheet 1 is to be replaced with the attached 1 sheet of drawing, showing Figure 1 on the attached page.

Signed and Sealed this

Twenty-second Day of December, 2009

David J. Kappos

David J. Kappos
*Director of the United States Patent and Trademark Office*

UNITED STATES PATENT AND TRADEMARK OFFICE

CERTIFICATE OF CORRECTION

PATENT NO. : PP 20,377 P2
APPLICATION NO. : 12/215932
DATED : October 6, 2009
INVENTOR(S) : David W. Cain It is certified that error appears in the above-identified patent and that said Letters Patent is hereby corrected as shown below:

Drawing sheet 1 is to be replaced with the attached 1 sheet of drawing, showing Figure 1 on the attached page.

This certificate supersedes the Certificate of Correction issued December 22, 2009.

Signed and Sealed this

Twenty-seventh Day of April, 2010

David J. Kappos

David J. Kappos
*Director of the United States Patent and Trademark Office*